United States Patent
Roos et al.

[11] Patent Number: 5,211,641
[45] Date of Patent: May 18, 1993

[54] DISPOSABLE ABSORBENT ARTICLES

[75] Inventors: Anders Roos, Onsala; Peter Rönnberg, Ravekarrsgatan; Båard Eiterjord, Ojersbo, all of Sweden; Jonas Hermansson, Nussloch, Fed. Rep. of Germany

[73] Assignee: Molnlycke AB, Goteborg, Sweden

[21] Appl. No.: 776,245

[22] PCT Filed: May 31, 1990

[86] PCT No.: PCT/SE90/00376
§ 371 Date: Nov. 14, 1991
§ 102(e) Date: Nov. 14, 1991

[87] PCT Pub. No.: WO90/14814
PCT Pub. Date: Dec. 13, 1990

[30] Foreign Application Priority Data

May 31, 1989 [SE] Sweden .................. 8901965-7

[51] Int. Cl.⁵ .................................. A61F 13/15
[52] U.S. Cl. .................................. 604/385.1
[58] Field of Search ........... 604/358, 378, 379, 385.1, 604/387

[56] References Cited
U.S. PATENT DOCUMENTS

| | | | |
|---|---|---|---|
| 2,747,575 | 5/1956 | Mercer | 604/385.1 |
| 3,768,479 | 10/1973 | Widlund | 604/366 |
| 3,874,385 | 4/1975 | Gellert | 604/385.1 X |
| 3,875,943 | 4/1975 | Fischer | 604/359 |
| 3,913,578 | 10/1975 | Schaar | 604/385.1 X |
| 3,929,134 | 12/1975 | Karami | 604/385.1 X |
| 4,475,913 | 10/1984 | Hlaban | 604/387 |
| 4,576,596 | 3/1986 | Jackson et al. | 604/385.1 X |
| 4,655,759 | 4/1987 | Romans-Hess et al. | 604/385.1 |
| 4,685,914 | 1/1987 | Holtman | 604/367 X |
| 4,787,896 | 11/1988 | Houghton et al. | 604/385.1 |

Primary Examiner—Randall L. Green
Assistant Examiner—Mary Beth O. Jones
Attorney, Agent, or Firm—Young & Thompson

[57] ABSTRACT

A disposable absorbent article, such as a diaper, an incontinence guard or the like, includes an inner, liquid-permeable casing sheet, which when the article is worn lies nearest the body of the wearer, an outer, liquid-impermeable casing sheet, an absorbent pad enclosed between the two casing sheets, and a layer of fibre wadding disposed between the absorbent pad and the inner casing sheet. The inner casing sheet is joined to the absorbent pad along two longitudinal lines forming permanent fold lines which divide the article, over at least a part thereof, into a central elongated part and two edge-parts located symmetrically on respective sides of the central elongated part. Each edge-part is folded between the respective fold line and its lateral edge such as to form an inwardly upstanding longitudinal fold in the outer casing sheet. The article has mutually opposed portions in the longitudinal folds, which portions are permanently joined to each other, whereby the edge-parts form inwardly upstanding embankment walls.

4 Claims, 3 Drawing Sheets

DISPOSABLE ABSORBENT ARTICLES

The present invention relates to a disposable absorbent article, such as a diaper, an incontinence guard or like article, which comprises a liquid-permeable casing layer, which when the article is worn lies nearest to the wearer's body, a liquid-impermeable casing sheet or backing sheet, and an absorbent pad enclosed between the two casing sheets.

Disposable absorbent articles, such as children's diapers or diapers which are intended for use as incontinence guards by adults, are normally constructed of a nonwoven layer through which the urine excreted passes, an absorbent layer of, for instance, cellulose fluff, optionally combined with so-called superabsorbents, and a liquid-impervious layer of polyethylene, for instance. For reasons of a process-technical nature, such articles have most often a flat, rectangular configuration, although such product configurations are not preferable in view of the fact that the body contours of the user are anything but flat.

In order to avoid lateral leakage through the sides of the article when worn, it is important that the article does not become folded or wrinkled so that liquid is able to run out through the sides of the article. The problem associated with the formation of folds and wrinkles is, naturally, pronounced when the wearer walks, sits down or moves in any other way, since the thighs of the wearer subject the article to external pressures sufficiently great to deform markedly the absorbent pad incorporated in the article, mainly in its transverse direction. It is thus important to configure the article such that the crotch region thereof will be relatively narrow. By crotch region is meant that region of the article which is intended to be located between the user's thighs when the article is worn. Since it is precisely the crotch region of the article which is responsible for receiving the largest amount of liquid excreted, it is extremely important that this crotch region, despite being narrow, is able to collect and absorb the liquid rapidly and effectively, while obtaining a good lateral seal at the same time.

The problem of lateral leakage cannot be solved solely by so shaping the article in manufacture that its crotch region will be narrower than its front and rear end respectively, since even in this case the article has a flat configuration and is consequently still wrinkled or folded in the crotch region when the absorbent pad is folded along the body of the person wearing the article. Although the liquid-permeable outer materials, essentially nonwoven materials, commercially available at present and used in sanitary products of the type diapers and incontinence guards, will allow a certain amount of liquid to pass rapidly therethrough, when the liquid is excreted quickly in large quantities, as is particularly the case with adult incontinence, part of this liquid will remain on top of the surface material and is therewith able to leak through any folds or wrinkles located between the absorbent pad and the user's body. This is because the absorbent material used predominantly in present day absorbent products, namely cellulose fluff, comprises fibres which are so fine that the cavities therebetween become quickly filled locally with liquid, with the result that liquid which remains unabsorbed cannot be absorbed by the material immediately but must remain on top of the surface material.

A sanitary product must also be able to receive and retain a large quantity of liquid while subjected to external forces, both during the time taken for the liquid to penetrate the liquid-permeable outer material and subsequent to the liquid having been absorbed by the absorbent pad.

When manufacturing such articles, it is known to fold the outer, elongated parts of an initially flat and rectangular diaper in towards the central elongated part thereof. The intention is to obtain a crotch region which is narrower than the ends of the diaper. Such diapers are referred to generally as wing-folded diapers and an example of one such diaper is described and illustrated in the U.S. Pat. No. 3,875,943. However, despite all, a wing-folded diaper is to be considered flat and can thus still be folded or wrinkled in the diaper crotch region, which can extend out as far as the side edges of the diaper and therewith cause leakage. Another drawback with wing-folded diapers is that it is necessary for the user to extend the inwardly folded side-parts at the diaper ends when wishing to use the diaper, which naturally complicates handling of the product.

Diapers which are cut to provide crotch regions narrower than the diaper end-parts are known, e.g., from U.S. Pat. No. 2,627,858. Such diapers are referred to generally as hour-glass diapers. Other diaper configurations include the T-configuration known, for instance, from U.S. Pat. No. 3,768,479. All of these diaper configurations are concerned with the body configuration of the wearer in the crotch region, but nevertheless present a flat shape and, similarly to the wing-folded diapers, are therewith poorly adapted to the shape of the wearer's body in general and the flat absorbent body is liable to be folded or wrinkled in its transverse direction when folded upwards around the body of the wearer.

U.S. Pat. No. 4,685,914 describes another embodiment of a diaper or incontinence guard in which an absorbent pad or body is applied in the form of a boat-shaped foamed-polyethylene shell. The use of a separate outer basin as a liquid-impervious casing is both expensive and complicated, however.

The U.S. Pat. No. 4,655,759 teaches a method of providing sanitary towels with embossed channels along which the longitudinally extending edge-parts of the towel can be folded-up to form a kind of container, therewith reducing the risk of leakage.

However, the fact is that wrinkling or folding of the sanitary towel occurs solely as a result of the pressure exerted by the wearer's thighs against the towel in its transverse direction. Consequently, it is more or less by chance that a truly leakage-proof region can be formed between the embossed channels. The edge-parts of the towel can, in principle, be curved or likewise deformed in any manner whatsoever when subjected to the force of the wearer's thighs and consequently there is no guarantee whatsoever that a leakage-proof region will be obtained. In comparison with an incontinence guard and a diaper, a sanitary towel is intended to absorb much less liquid and is subjected to much smaller liquid flows.

The present invention relates to the provision of absorbent articles such as diapers, or incontinence guards, which are anatomically configured, which have a large liquid-collecting capacity both before and after absorption, which can absorb liquid rapidly, and which can be produced continuously at high production speeds and at low cost, with the aid of simple production means and without appreciable material wastage.

An inventive absorbent product is characterized mainly by at least two fold lines which extend permanently in the longitudinal direction of the article and which divide the article, over at least a part thereof, into a central longitudinally extending part and edge-parts located symmetrically on respective sides of said central part.

With the aid of simple manufacturing methods, the invention enables a product to be produced which presents a desired three-dimensional structure, starting from a flat blank comprising all materials incorporated in an absorbent article. Thus, it is not necessary to manufacture a separate, injection-moulded foamed-plastic shell, such manufacture requiring a plurality of additional process stages and rendering manufacture more expensive and more difficult to carry out.

Furthermore, upward-folding of the edge-parts results in the formation of liquid-enclosing embankments along the fold lines, these embankments forming, at the same time, the main contact surface of the article with the body of the user in that region of the article in which the fold lines are located, such as to enable a large quantity of liquid excreted at one and the same time to be collected in an elongated, dammed central part of the inventive article.

The liquid is, in this way, held removed from the user at the same time as the dammed, central part of the article provides an effective barrier against leakage of liquid still not absorbed.

There are primarily two properties which are important to an absorbent article, namely that the article is able to absorb large quantities of liquid secreted momentarily, without liquid running over the edges of the article, and that the article will present a dry surface to the wearer subsequent to absorption. An article constructed in accordance with the invention contains both of these properties, in addition to several other properties desirable in the case of an absorbent article, such as comfort and discretion in wear.

An absorbent article constructed in accordance with the present invention will now be described in more detail with reference to an exemplifying embodiment thereof illustrated in the accompanying drawings.

Figure 1:
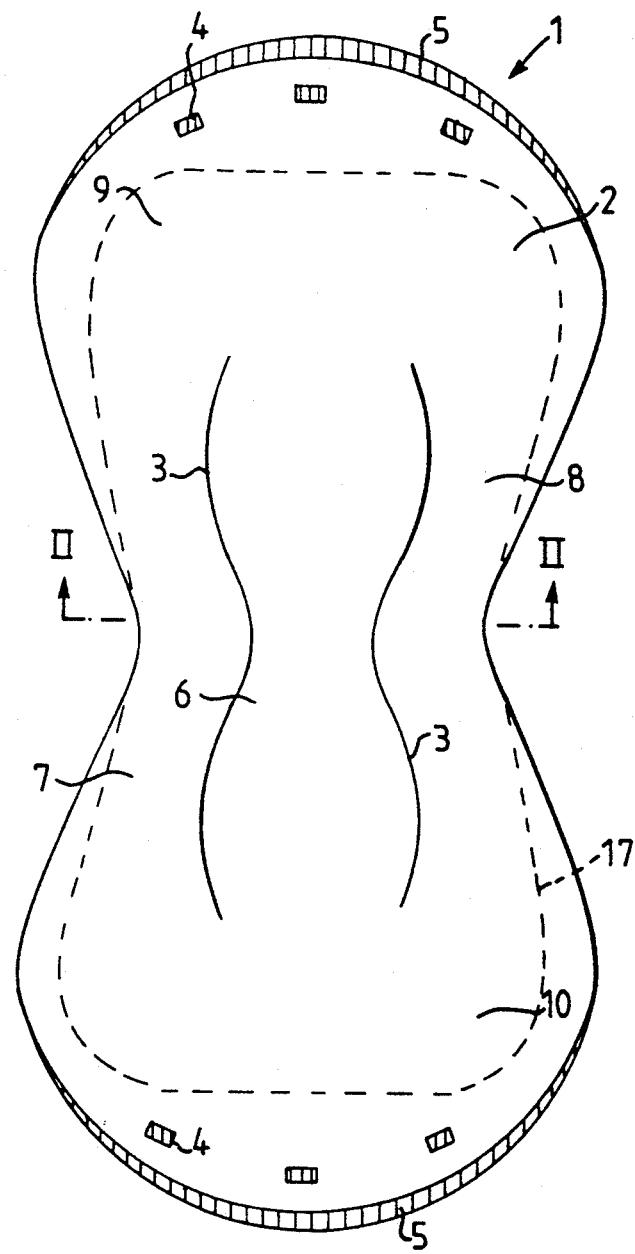
FIG. 1 is a view of an inventive absorbent article taken from above, with the side of the article intended to face towards the wearer facing towards the viewer.

FIG. 1 illustrates an absorbent article 1. The article 1 comprises a liquid-permeable sheet 2, made of a nonwoven fibre material, attached as surface material nearest the body of the wearer.

The sheet 2 is joined with an underlying absorbent pad by means of two, longitudinally extending sinusoidal fold lines 3, e.g. weld joins or adhesive joins, said fold lines 3 functioning to divide the article 1 into a central part 6 and two edge-parts 7, 8. The parts 6, 7 and 8 are relatively elongated, i.e. their extension in the longitudinal direction of the article is greater than their extension in the transverse direction thereof. As will be seen from the Figure, the back and front end-parts 9, 10 are of mutually identical configuration and are provided with a plurality of discrete joins 4 and joins 5 which end-seal the end-parts 9, 10. The joins 4, 5 may be seam welds or adhesive bonds, for instance.

When the fold lines are formed by seam welds, the seams can be produced by any conventional welding technique whatsoever, e.g. by ultrasonic welding, impulse welding or high frequency welding.

The illustrated fold lines 3, are not restricted to the sinusoidal curve pattern illustrated in FIG. 1, but may be linear or arcuate in configuration. Preferably, two fold lines 3 are provided, although it is also conceivable to provide solely one fold line or a number of fold lines greater than three.

According to one embodiment of the invention (not shown) in order to increase the flexibility of the article, the fold lines may be formed by two punctiform seams disposed along a continuous curve and forming a pattern similar to that formed by the fold lines in FIG. 1, or any other desired pattern whatsoever. Neither is the scope of the invention restricted by the lengths of said fold lines. However, the fold lines shall be positioned so that the liquid-receiving part of the article, the so-called wetting location, is framed by the edge-parts 7, 8 and therewith constitutes a region of the central part 6. It should be mentioned in this connection that the distance between the fold lines 3 may have any desired value and does not therefore limit the scope of the invention.

The seams or joins 4 in respective end-parts 9, 10 may be smaller or greater than three in number and may also be excluded totally. Similar to the fold lines 3, the seams 4 may have the form of discrete punctiform weld-bonds or may comprise continuous, curved seams where the shape of the curve is optional. The seams 4 result in a smaller article contact-surface with the body of the wearer, therewith enhancing the comfort of the article when worn.

Figure 2:
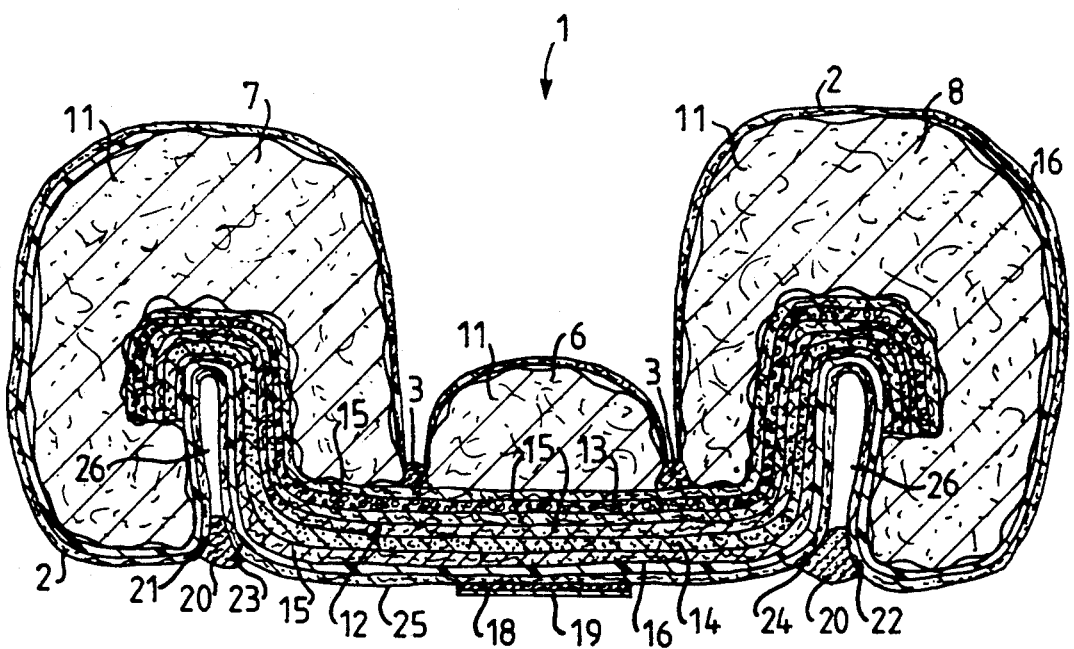
FIG. 2 is a sectional view of the absorbent article illustrated in FIG. 1, taken on the line II—II of said Figure.

FIG. 2 illustrates an example of upward-folding of the edge-parts 7, 8 in accordance with the invention. The expression "upward-folding" as used here includes all manner of folding or bending of the edge-parts which will cause the edge-parts located externally of the fold-lines, when viewed as a whole, to form upstanding embankments or like walls in relation to the central part, seen in a direction towards the wearer. For instance, as illustrated in FIG. 2, the edge-part can be folded double in its longitudinal direction, wherewith the outer longitudinally extending part will be folded in a direction away from the wearer. Appropriate fixation of the fold will result in a reduction in the transverse extension of the edge-parts, causing an increase in the vertical extension or height extension of said edge-parts, such that the edge-parts form upstanding embankment walls.

Located immediately beneath the liquid-permeable sheet 2 is fibre wadding body 11. This wadding functions to receive the liquid excreted and to permit the liquid to pass rapidly therethrough. The wadding is preferably loosely packed and is resilient in both its dry and its wet state. The fibre wadding 11 may comprise, for instance, thermoplastic, weldable fibres, such as polyester, polypropylene or polyethylene fibres or mixtures thereof. So-called bicomponent fibres are suitable materials in this regard, by which is meant fibres which comprise two kinds of polymer, for instance polypropylene/polyethylene, polyester/polyester or polyester/polyethylene. The fibre wadding 11 may be either a woven or non-woven structure, without departing from the inventive concept. Heat and binding agents are examples of the means by which a fibre wadding structure can be bound. The adhesive bonding agent may, for instance, be latex. The wadding may also be hydrophobic or hydrophilic. It will be understood that natural fibres which exhibit the aforesaid properties can also be used.

An absorbent pad 12 located beneath the wadding comprises two layers of superabsorbent material 13, 14 which is placed in powder form between a plurality of tissue layers 15. The superabsorbent material may have a form other than powder, e.g. may have the form of fibres. By superabsorbent material is meant a material which can absorb a liquid quantity corresponding to several times its own weight. The superabsorbents in respective layers differ essentially with regard to absorption properties, absorption rates and liquid-retention abilities when subjected to pressure. The superabsorbent in layer 14 has a very high absorption rate, whereas the superabsorbent in layer 13 has a very pronounced ability to retain liquid when subjected to pressure. Each of the tissue layers 15 may comprise one or more layers of tissue. It is also conceivable to use other types of carrier material than tissue, for instance nonwoven material.

Placed beneath the absorbent pad 12 and between said pad and the liquid-permeable sheet 2 extending peripherally around the whole of the article is a liquid-impermeable sheet 16 made, for instance, of polyethylene or polypropylene. The liquid-permeable sheet 2 is joined to the liquid-impermeable sheet 16, e.g., with the aid of an adhesive binder, whereas the fibre wadding 11 is neither connected to the liquid-permeable sheet 2 nor to the liquid-impermeable sheet 16, with the exception of the seam or join locations 3, 4 and 5. The liquid-impermeable sheet 16 extends upwards to some extent along the upwardly raised edge-part 7, 8 which provides additional protection against leakage from the sides of the article. The layer 16 extends around the margins of the end-parts 9, 10 and slightly inwardly thereof, as indicated by a broken line 17 in FIG. 1.

The edge-parts 7, 8 are joined in a double-fold, by means of a bonding means 20, for instance by means of an adhesive binding agent or a punctiform weld, a region 21, 22 of the liquid-permeable sheet 2 being joined with another region 23, 24 of said sheet within the same respective edge-parts 7, 8 on the side surface of the article 1 facing away from the user, i.e. the underside 25 of said article The binding agent is, for instance, applied in the form of one or more glue points. The punctiform weld-joins may be one or more in number.

When the edge-parts 7, 8 are folded in this manner and fixated to the underside 25 of the article, the edge-parts 7, 8 of the article impart to the central part of said article, as seen in its cross-direction, a convex shape, at the same time as said edge-parts 7, 8 are erected to a raised position in relation to the central part 6 as seen in the height extension of the article. When the article is in use, the wearer's thighs will press the edge-parts 7, 8 towards the central part 6, but because the edge-parts 7, 8 in their upwardly raised positions curve inwardly towards the central part 6, the occurring pressure forces will accentuate still further the damming effect of the central part 6 and counteract the tendency of the edge-parts 7, 8 to gape. Thus, in accordance with the present invention, the apparently disadvantageous fact that the thighs of the wearer will deform the article in its transverse direction is utilized in a beneficial manner to provide a considerably improved absorbent product or article, both from the aspect of liquid collection and leakage. The edge-parts 7, 8 can be folded and fixated in a number of ways within the scope of the following claims.

By constructing the inventive article from materials other than those conventionally used, it is not only possible to obtain a three-dimensional article by folding up the edge-parts of the article along said fold lines, but also to obtain considerably improved liquid-retention and a drier abutment surface against the wearer's skin than in the case of traditionally constructed absorbent pads in which the absorption material is mainly cellulose fluff. The fibres of cellulose fluff normally have the drawback of discharging absorbed liquid when subjected to pressure, causing the surface material closest to the wearer's body to become moist or wet, and therewith resulting in increased discomfort for the wearer. As a result of placing fibre wadding immediately beneath the liquid-impermeable surface material, the article will obtain a dry surface while, at the same time, the wadding will provide a soft and comfortable layer of material against the wearer's skin. The structure of the fibre wadding includes very coarse capillaries in comparison with the cellulose fluff, and consequently liquid will be transported very rapidly in the fibre wadding.

Furthermore, the fibre wadding alienates the liquid absorbed in the absorbent pad from the body of the wearer, wherein the surface of the absorbent article will be felt to be dry and comfortable, even when the article has been in use for some time. The fibre wadding also contributes towards configuring the article.

By choosing suitable material, it is possible to produce in the voluminous bulky wadding layer a durable bond between surface material, fibre wadding and absorbent pad, or, as seen from the side of the article remote from the wearer, between surface material, plastic-barrier layer and absorbent pad, e.g. by gluing or welding. Because the fibre wadding comprises thermoplastic fibres and is also highly voluminous, the application of joins or seams therein will form in the bulky wadding deep, distinctive fold lines, outside of which the edge-parts of the article are folded-up so as to dam in the central part of the article located between said edge-parts, said edge-parts being fixated in their upwardly raised positions in relation to said central part.

Attached to the underside 25 of the article is an adhesive layer or strip 18, by means of which the article can be removably fastened to the user's underclothes when wearing said article Prior to use, this adhesive layer 18 is protected by a protective strip 19, which is preferably treated with a release agent on the side thereof facing the adhesive layer 18 and which can be readily removed when the article 1 is to be worn, so as to expose the adhesive layer 18 for active use.

Figure 3:
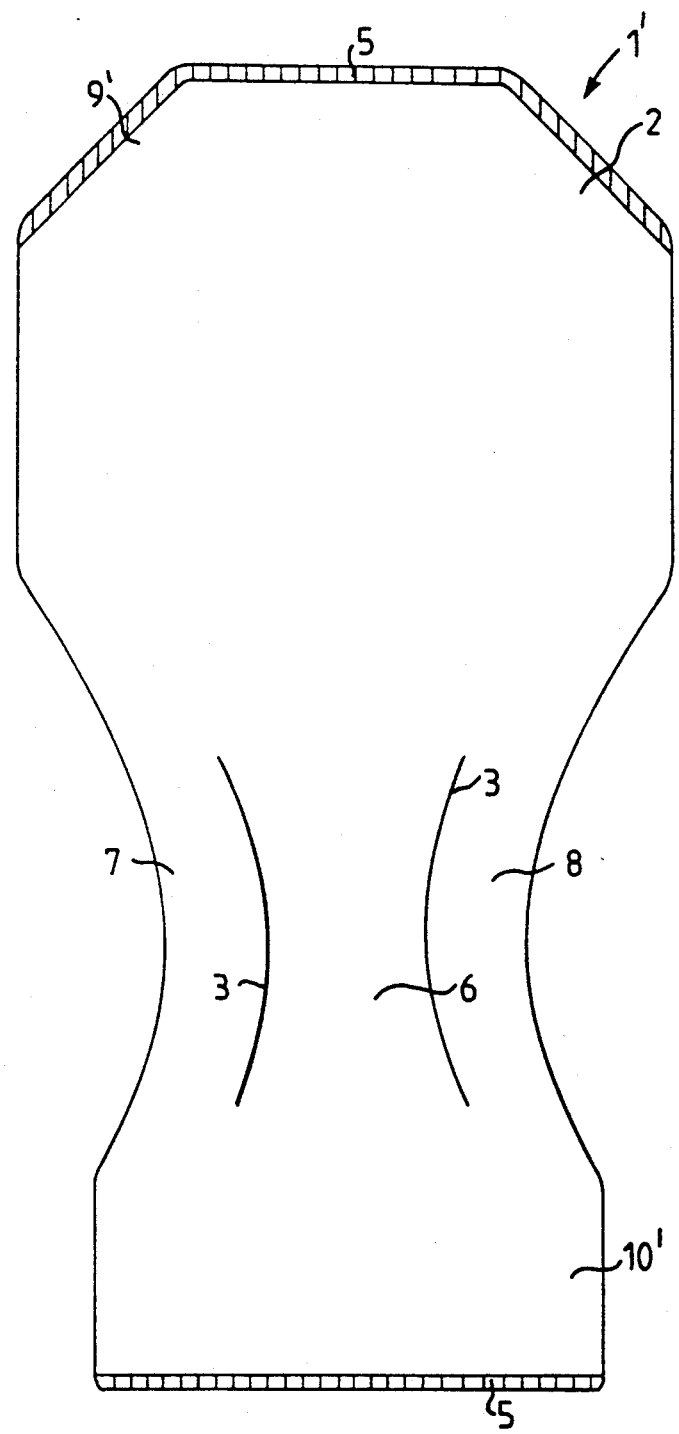
FIG. 3 is a view of a further embodiment of an inventive article taken from above, with the side of the article intended to face the wearer facing towards the viewer.

FIG. 3 illustrates another embodiment of an absorbent article, here referenced 1'. Similarly to the article 1, the article 1' incorporates a liquid-permeable sheet 2, which is located nearest the wearer, two longitudinally extending fold lines 3, a central part 6, two edge-parts 7, 8, and end-seals 5 which seal-off the end-parts 9', 10' of said article. The rear end-part 9' is much larger than the front end-part 10', so as to be able to receive faeces. Because of its enlarged end-part 9', the article 1' is able to enclose a larger absorbent pad than the article 1 of the embodiment before described, thereby enabling the article 1' to absorb much larger quantities of liquid than those for which the article 1 is intended, for instance adult incontinence.

A number of modifications are conceivable within the scope of the claims.

For instance, fold lines may also be provided on the underside of the article, with the intention of further amplifying the fold lines produced on the upper side thereof. Naturally, a layer of fibre wadding can also be positioned between the absorbent pad and the liquid-impermeable sheet in this case. Thus, all of the material incorporated in the article can be joined together along the fold lines in conjunction therewith.

The methods by which the fold lines, for instance, seaming, glueing, welding, can also be combined. For instance, the liquid-permeable sheet can be welded to the fibre wadding while glueing the wadding to the absorbent pad along the fold lines are formed.

In addition to the absorbent pad described with reference to the illustrated exemplifying embodiments, a number of other absorbent pad constructions known to the person skilled in this art may be incorporated in the inventive article. For instance, the absorbent pad described with reference to FIG. 2 may be supplemented with a number of layers of tissue or the like placed on one or both sides of the absorbent body. It is also possible to use an absorbent pad made of cellulose fluff, optionally with superabsorbents mixed therein. The absorbent pad may also have admixed therein material which has no absorbing function, but which serves to improve binding to the surrounding thermoplastic sheets. Such material may, for instance, comprise melt fibres. As will be understood, the fibre wadding may be totally excluded if so desired, in which case the article will solely include an absorbent body comprising cellulose fluff, with or without superabsorbents or other absorbent material.

We claim:

1. A disposable absorbent article, such as a diaper, an incontinence guard or the like, comprising an inner, liquid-permeable casing sheet, which when the article is worn lies nearest the body of the wearer, an outer, liquid-impermeable casing sheet, an absorbent pad enclosed between the inner and outer casing sheets, and a layer of fibre wadding disposed between the absorbent pad and the inner casing sheet, the inner casing sheet being joined to the absorbent pad along two longitudinal lines forming permanent fold lines which divide the article, over at least a part thereof, into a central elongated part and two edge-parts located symmetrically on respective sides of the central elongated part, and each edge-part being folded between the respective fold line and its lateral edge such as to form a longitudinal fold in the outer casing sheet, said fold being upstanding in a direction toward the body of the wearer, said article having mutually opposed portions in said longitudinal folds, which portions are permanently joined to each other, whereby the edge-parts form inwardly upstanding embankment walls.

2. An article (1, 1') according to claim 1, wherein the fibres of the fibre wadding (11) are from a group consisting of polyester, polypropylene, polyethylene fibres and mixtures thereof.

3. An article (1, 1') according to claim 1, wherein the fold lines (3) comprise seam welds.

4. An article (1, 1') according to claim 1, wherein the fold lines (3) comprise adhesive bonds.

* * * * *